United States Patent [19]

Tsuyutani et al.

[11] Patent Number: 5,883,280
[45] Date of Patent: Mar. 16, 1999

[54] PROCESS FOR THE PREPARATION OF PHOSPHORIC MONOESTER

[75] Inventors: Shinji Tsuyutani; Kengo Shibata; Kiyoshi Aimono, all of Wakayama, Japan

[73] Assignee: Kao Corporation, Tokyo, Japan

[21] Appl. No.: 793,805

[22] PCT Filed: Sep. 20, 1995

[86] PCT No.: PCT/JP95/01890

§ 371 Date: Mar. 20, 1997

§ 102(e) Date: Mar. 20, 1997

[87] PCT Pub. No.: WO96/09305

PCT Pub. Date: Mar. 28, 1997

[30] Foreign Application Priority Data

Sep. 20, 1994 [JP] Japan ................................ 6-224593

[51] Int. Cl.$^6$ .................................................. C07F 9/02
[52] U.S. Cl. ............................................................ 558/110
[58] Field of Search ............................................... 558/110

[56] References Cited

U.S. PATENT DOCUMENTS

| | | | |
|---|---|---|---|
| 3,146,255 | 8/1964 | Nelson et al. | 558/110 |
| 3,318,982 | 5/1967 | Klose et al. | 558/110 |
| 4,126,650 | 11/1978 | Via et al. | |
| 4,350,645 | 9/1982 | Kurosaki et al. | |
| 4,670,575 | 6/1987 | Kurosaki et al. | |
| 4,874,883 | 10/1989 | Uphues et al. | 558/110 X |
| 5,550,274 | 8/1996 | Reierson | 558/110 |

FOREIGN PATENT DOCUMENTS

| | | |
|---|---|---|
| 41-14416 | 8/1966 | Japan . |
| 42-6730 | 3/1967 | Japan . |
| 43-26492 | 11/1968 | Japan . |
| 50-064226 | 5/1975 | Japan . |
| 62-033190 | 2/1987 | Japan . |
| 1121683 | 8/1968 | United Kingdom . |

OTHER PUBLICATIONS

Patent Abstracts of Japan, vol. 11, No. 214 (C–434) Jul. 10, 1987, & JP,A 62 033 190 (Miyoshi Oil & Fat Co. Ltd.) Feb. 13, 1987.

*Primary Examiner*—Michael G. Ambrose
*Attorney, Agent, or Firm*—Oblon, Spivak, McClelland, Maier & Neustadt, P.C.

[57] ABSTRACT

An organic hydroxyl compound is reacted with polyphosphoric acid under such conditions that the ratio, as defined by formula (1), has a value exceeding 3.2; and phosphorus pentaoxide is added to the reaction product thus obtained in such an amount that the ratio, as defined by formula (1), has a value in the range of from 2.8 to 3.2:

$$\frac{\left(\begin{array}{c}\text{Molar amount of water}\\\text{included in the}\\\text{polyphosphoric acid}\\\text{represented as} P_2O_5 \cdot nH_2O\end{array}\right) + \left(\begin{array}{c}\text{Molar amount of}\\\text{organic hydroxyl}\\\text{compound}\end{array}\right)}{\left(\begin{array}{c}\text{Molar amount of phosphorylating}\\\text{agent(s) represented as } P_2O_5\end{array}\right)} \quad (1)$$

If necessary, the obtained reaction product is deodorized by the removal of the organic hydroxyl compound unreacted therefrom. The process does not give any product of high-viscous gel and therefore enables the industrially easy manufacture of a phosphoric monoester having an extremely high purity, a lowered orthophosphoric acid content, and a good odor.

2 Claims, 2 Drawing Sheets

PROCESS FOR THE PREPARATION OF PHOSPHORIC MONOESTER

BACKGROUND OF THE INVENTION

1. Field of the Invention

The present invention relates to a process for the preparation of a phosphoric monoester through the phosphorylation of an organic hydroxyl compound. More particularly, the present invention relates to a process for the preparation of a phosphoric monoester which can easily provide a phosphoric ester mixture having a high phosphoric monoester purity, a reduced orthophosphoric acid content and good odor.

2. Description of the Related Art

Phosphoric esters of organic hydroxyl compounds are used in a wide field as a detergent, a textile treating agent, an emulsifying agent, a rust inhibiter, a liquid ion exchanger and a medicament.

Although the reaction of an organic hydroxyl compound with phosphorus pentaoxide has been known as an industrial process for the preparation of phosphoric esters in the prior art, the product of the reaction comprises mainly a nearly equimolar mixture of a phosphoric monoester represented by the following formula (A) and a phosphoric diester represented by the following general formula (B) (hereinafter, this mixture is referred to as "sesquiphosphate"):

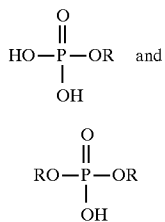

wherein R represents a linear or branched alkyl or alkenyl group having 6 to 30 carbon atoms.

There are great differences in properties between a phosphoric monoester and a phosphoric diester. To give an explanation about, e.g., alkali metal salts and alkanolamine salts of long-chain alkyl phosphates, phosphoric monoester salts are soluble in water, excellent in foaming power and detergency, less toxic and lowly irritant to the skin to be useful as an excellent detergent, while phosphoric diester salts are little soluble in water and exhibit little foaming power or rather have defoaming properties, and accordingly they can not be used as high foaming detergents. Therefore, when sesquiphosphate salts are employed, the above performances inherent in phosphoric monoester salts can not be exhibited, and, therefore, sesquiphosphate salts are unusable as substitutes for phosphoric monoester salts.

Under these circumstances, the development of a process by which a phosphoric ester mixture having a high phosphoric monoester content can be prepared on an industrial scale safely and easily has been eagerly expected and the following processes have been reported to answer this expectation:

(1) a process which comprises reacting an organic hydroxyl compound with phosphorus oxychloride and hydrolyzing the obtained monoalkyl phosphorodichloridate;

(2) a process which comprises adding water to an organic hydroxyl compound and thereafter adding phosphorus pentaoxide to the obtained mixture to conduct phosphorylation with the amount of water preliminarily added being 0.5 to 3 mol per mol of phosphorus pentaoxide;

(3) a process which comprises reacting an organic hydroxyl compound with orthophosphoric acid and phosphorus pentaoxide;

(4) a process which comprises reacting an organic hydroxyl compound with a condensed phosphoric acid (polyphosphoric acid);

(5) a process which comprises reacting an organic hydroxyl compound with phosphorus pentaoxide in the presence of water while blowing steam into the reaction system; and (6) a process which comprises reacting an organic hydroxyl compound with a phosphorylating agent mixture comprising phosphorus pentaoxide, phosphoric acid and a polyphosphoric acid under such a condition that phosphoric acid components are excess, adding an organic hydroxyl compound to the obtained reaction mixture to make up to a stoichiometric amount and conducting further phosphorylation [see U.S. Pat. No. 4,350,645 (published on Sep. 21, 1982, assignee: Kao Corporation)].

However, these processes have respective disadvantages as will now be described, being unsatisfactory as industrial processes for the preparation of phosphoric ester mixtures.

The process (1) gives hydrogen chloride as a by-product to be significantly problematic in the corrosion of equipment and the disposal of hydrochloric acid. Further, this process involves the formation of an alkyl chloride as a by-product, so that it is difficult to enhance the phosphoric monoester content of the reaction product.

According to the processes (2) and (3), the ratio of the phosphoric monoester to the phosphoric diester in the reaction product can be enhanced by increasing the amount of water or orthophosphoric acid used. However, the use of a large amount of water or orthophosphoric acid remarkably lowers the degree of conversion of phosphorus to give a remarkably increased amount of orthophosphoric acid. The contamination of the product with a large amount of orthophosphoric acid has undesirable influence on some fields, so that the use field of the product is limited.

According to the process (4), a phosphoric monoester can be prepared selectively. However, the process (4) as well as the processes (2) and (3) gives a large amount of orthophosphoric acid as a by-product. To decrease the amount of orthophosphoric acid formed as a by-product according to the process (4), it is necessary to use a polyphosphoric acid having an extremely high degree of condensation. However, such a polyphosphoric acid is in the form of a high-viscosity gel, which necessitates the use of an industrially special reactor and makes the manufacture difficult.

According to the process (5), the ratio of the phosphoric monoester to the phosphoric diester is enhanced by blowing steam into the reaction system. However, the blowing of steam into the reaction system increases the amount of orthophosphoric acid formed. As described above, the contamination of the product with a large amount of orthophosphoric acid has undesirable influence on some fields, so that the use field of the product is limited.

According to the process (6), only a small amount of an organic hydroxyl compound is present in the reaction system in the early stages of the reaction, so that the phosphoric monoester/phosphoric diester ratio of the reaction product is enhanced. However, when the amount of an organic hydroxyl compound used in the early stages lies within a certain range, the reaction product takes the form of a high-viscosity gel to necessitate the use of an industrially special reactor. In some cases according to the process (6), additionally, the decomposition of the phosphoric monoester formed proceeds, so that the yield of the phosphoric monoester is lowered with an increase in the orthophosphoric acid content of the reaction product. The increase in the orthophosphoric acid content has undesirable influence on some fields, so that the use field of the resulting product is limited.

DISCLOSURE OF THE INVENTION

SUMMARY OF THE INVENTION

An object of the present invention is to provide a process for the preparation of a phosphoric monoester having good odor, an extremely high purity and a lowered orthophosphoric acid content, which does not give any product of high-viscosity gel over all of the stages of the process (including the intermediate stages) and therefore can be easily conducted industrially.

According to any of the processes of the prior art as described above, it was difficult to prepare a high-purity phosphoric monoester having a lower orthophosphoric acid content without the gelation of the reaction product. The present inventors have made extensive studies to improve the processes for the preparation of phosphoric monoesters according to the prior art. As a result of the studies, they have found that when an organic hydroxyl compound is first reacted with polyphosphoric acid as phosphorylating agent of which the amount is smaller than the stoichiometric one to conduct a reaction without gelation; phosphorus pentaoxide is added to the obtained reaction product in such a way that the total amount of both phosphorylating agents reaches a nearly stochiometric amount for the organic hydroxyl compound; and the reaction is further advanced, a phosphoric monoester which has a low orthophosphoric acid content and good odor can be prepared in an extremely high yield. The present invention has been accomplished on the basis of this finding.

Thus, the present invention provides a process for the preparation of a phosphoric monoester by reacting an organic hydroxyl compound with phosphorus pentaoxide and polyphosphoric acid as phosphorylating agents, comprising:

(1) a first step of reacting an organic hydroxyl compound with polyphosphoric acid under such conditions that the ratio, as defined by formula (1), has a value exceeding 3.2, and (2) a second step of adding phosphorus pentaoxide in such an amount that the ratio, as defined by formula (1), has a value in the range of from 2.8 to 3.2:

$$\frac{\left(\begin{array}{c}\text{Molar amount of water}\\ \text{included in the}\\ \text{polyphosphoric acid}\\ \text{represented as} P_2O_5.nH_2O\end{array}\right) + \left(\begin{array}{c}\text{Molar amount of}\\ \text{organic hydroxyl}\\ \text{compound}\end{array}\right)}{\left(\begin{array}{c}\text{Molar amount of phosphorylating}\\ \text{agent(s) represented as } P_2O_5\end{array}\right)}. \quad (1)$$

The term "molar amount of organic hydroxyl compound" means the equivalent of hydroxyl group(s) derived from the organic hydroxyl compound.

In other words, the present invention relates to a process for the preparation of a phosphoric monoester by reacting phosphorus pentaoxide and polyphosphoric acid as phosphorylating agents with an organic hydroxyl compound, characterized in that polyphosphoric acid is reacted with an organic hydroxyl compound under such conditions that the value represented by the following formula (2) exceeds 3.2 and thereafter phosphorus pentaoxide is added to the obtained reaction product to conduct a reaction under such conditions that the value represented by the formula (2), wherein the denominator is the total amount of the above polyphosphoric acid and the phosphorus pentaoxide, comes to be from 2.8 to 3.2:

$$\frac{\left(\begin{array}{c}\text{molar number of}\\ \text{organic hydroxyl}\\ \text{compound added}\end{array}\right) + \left(\begin{array}{c}\text{molar number of water}\\ \text{in the case where}\\ \text{polyphosphoric acid is}\\ \text{represented by } P_2O_5 \cdot nH_2O\end{array}\right)}{\left(\begin{array}{c}\text{molar number of phosphorylating}\\ \text{agent(s) calculated as } P_2O_5\end{array}\right)}. \quad (2)$$

The first step is generally conducted under such conditions that the ratio, as defined by formulae (1) or (2), has a value in the range of from above 3.2 to 20, preferably under such conditions that the ratio has a value in the range of from 4.0 to 10.

The second step according to the present invention is preferably conducted under such conditions that the ratio, as defined by formulae (1) or (2), has a value in the range of from 2.9 to 3.1.

A polyphosphoric acid having a phosphoric acid concentration, calculated in orthophosphoric acid units (i.e., calculated as $H_3PO_4$), in the range of from 105 to 120% by weight is preferably used.

It is preferable that the above process for the preparation of a phosphoric monoester further comprises a step of hydrolyzing the reaction product and/or a step of removing the organic hydroxyl compound unreacted from the reaction product.

The removal of the organic hydroxyl compound unreacted is preferably conducted by steam distillation.

Further, the present invention also provides a phosphoric monoester obtainable by the process according to the present invention.

The present invention will now be described in detail.

DETAILED DESCRIPTION OF THE INVENTION

The phosphorus pentaoxide in the present invention is a compound called also "phosphoric acid anhydride" and the molecular formula thereof is $P_4O_{10}$ or $P_2O_5$.

The polyphosphoric acid is a condensate of orthophosphoric acid represented by formula (I) which will be described below, and has a pyrophosphate bond(s) (P—O—P) in the molecule. The polyphosphoric acid is generally one member selected from the group consisting of linear condensed phosphoric acids represented by formula (E) which will be described below, branched condensed phosphoric acids, cyclic condensed phosphoric acids and cyclic condensed phosphoric acids having a side chain, or a mixture of two or more of them. The polyphosphoric acid may also contain, as one component thereof, orthophosphoric acid represented by formula (I) which will be described below. Examples of the linear condensed phosphoric acids include pyrophosphoric acid represented by formula (C) which will be described below and tripolyphosphoric acid represented by formula (D) which will be described below. Examples of the branched condensed phosphoric acids, cyclic condensed phosphoric acids and cyclic condensed phosphoric acids having a side chain include compounds represented by the following formulae (F), (G) and (H) respectively:

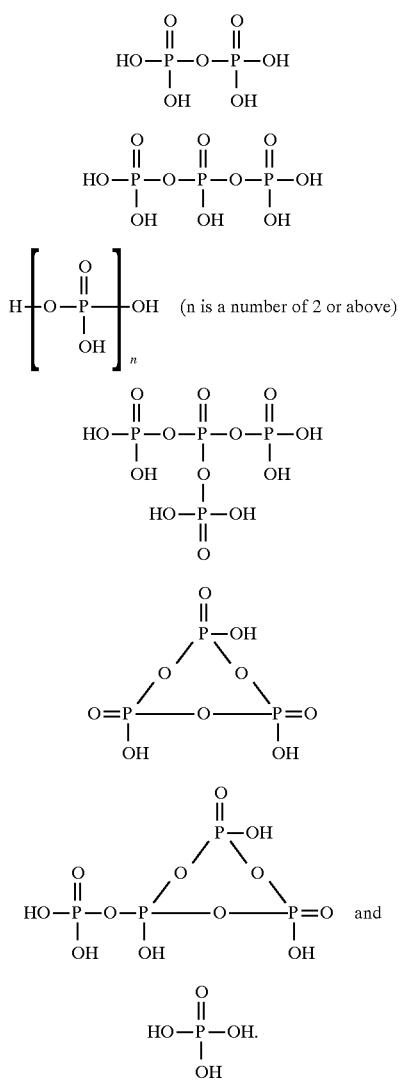

The phosphoric acid concentration of the polyphosphoric acid to be used in the present invention, calculated in orthophosphoric acid units (i.e., calculated as $H_3PO_4$), is preferably 105 to 120% by weight, still more preferably 110 to 118% by weight, in views of attaining an enhanced ratio of the phosphoric monoester to the phosphoric diester and the handling of the polyphosphoric acid, though the concentration is not particularly limited.

The organic hydroxyl compound to be used in the present invention is preferably an organic monohydroxyl compound represented by the formula: ROH, though it is not limited thereto as long as it is an organic hydroxyl compound having a hydroxyl group(s). Examples thereof include linear or branched, saturated or unsaturated alcohols having 6 to 30, preferably 8 to 24 carbon atoms, adducts of the alcohols with an alkylene oxide(s) (wherein the alkylene oxide has 2 to 4 carbon atoms and the number of alkylene oxide molecules added is 1 to 100), and adducts of alkylphenols (wherein the alkyl moiety has 6 to 20 carbon atoms) with an alkylene oxide(s) (wherein the alkylene oxide has 2 to 4 carbon atoms and the number of alkylene oxide molecules added is 1 to 100).

Specific examples of the organic hydroxyl compound include octanol, nonyl alcohol, decyl alcohol, undecyl alcohol, lauryl alcohol, tridecyl alcohol, myristyl alcohol, pentadecyl alcohol, cetyl alcohol, heptadecyl alcohol, stearyl alcohol, nonadecyl alcohol, 2-ethylhexanol, isooctanol, isononanol, isodecanol, isotridecanol and synthetic alcohols such as Oxo alcohol (a product of Nissan Chemical Industry Co. Ltd.), Diadol (a product of Mitsubishi Chemical Co. Ltd.), Dobanol (a product of Mitsubishi Petrochemical Co. Ltd.), Linevol (a product of Showa Shell Chemical Co. Ltd.), Neodol (a product of Shell) and Lial (a product of Eni Chem).

In the present invention, one of these organic hydroxyl compounds or a mixture of two or more of them may be used.

In the reaction of an organic hydroxyl compound with polyphosphoric acid (i.e., the first step), the order and method of feeding an organic hydroxyl compound and polyphosphoric acid are not particularly limited. From the standpoints of easiness of the removal of heat of reaction and mixing operation, however, it is preferable to feed the organic hydroxyl compound and polyphosphoric acid simultaneously to the reactor or to add polyphosphoric acid to the organic hydroxyl compound.

The above reaction must be conducted under such conditions that the ratio, as defined by the above formula (1), has a value exceeding 3.2, generally a value in the range of from above 3.2 to 20, preferably a value in the range of from 3.5 to 20, particularly preferably a value in the range of from 4.0 to 10. Under such conditions that the value is 3.2 or less, the polyphosphoric acid to be used will inevitably have a high degree of condensation. Such a polyphosphoric acid is extremely viscous and, therefore, the industrial phosphorylation with such a viscous polyphosphoric acid will necessitate the use of a special reactor and will not be easy to advance the reaction. In view of attaining an enhanced ratio of the phosphoric monoester to the phosphoric diester, it is desired that the above reaction is conducted under such conditions that the ratio, as defined by the above formula (1), has a value in the range of from above 3.2 to 20.

The reaction of an organic hydroxyl compound with polyphosphoric acid (the first step) is conducted at a temperature of generally 40° to 120° C., preferably 60° to 100° C., in views of attaining a suitable reaction rate and reducing the decomposition of the resulting esters. The first step is conducted for generally 0.2 to 12 hours, preferably 0.5 to 5 hours, in views of reducing the unreacted polyphosphoric acid content of the reaction product and improving the productivity.

Then, to the reaction product of the first step thus obtained, phosphorus pentaoxide is added in such an amount that the value represented by the above formula (1) comes to in the range of from 2.8 to 3.2, preferably 2.9 to 3.1 to further conduct phosphorylation. In this step, the phosphorus pentaoxide may be added at once or in portions. When the value represented by the formula (1) is less than 2.8, the resulting reaction product will contain a remarkably increased amount of the unreacted phosphoric acid, while when it exceeds 3.2, the resulting product will contain a remarkably increased amount of the unreacted organic hydroxyl compound to result in deteriorated odor, which necessitates the labor and equipment for deodorization unfavorably.

The reaction of the second step is conducted at a temperature of generally 40° to 120° C., preferably 60° to 100° C., in views of attaining a suitable reaction rate and reducing the decomposition of the resulting esters. The second step is conducted for generally 1 to 24 hours, preferably 5 to 15 hours, in views of improving the reaction rate of the organic hydroxyl compound and reducing the decomposition of the resulting esters.

Although the phosphoric monoester-containing reaction product prepared by the above process can be used as such, it is preferable that water be added to the reaction product to conduct hydrolysis. The reaction product obtained by the above process contains a compound having a pyrophosphate bond(s) and the pyrophosphate bond(s) is(are) cleaved by hydrolysis. The compound having a pyrophosphate bond(s) has adverse effects such as viscosity increase or gelation on a phosphoric monoester-containing product. In other words, the presence of a large amount of a compound having a pyrophosphate bond(s) in the reaction product, i.e., the contamination of the product with a large amount of such a compound, increases the viscosity.

In the above hydrolysis, it is preferable to use water in an amount of 1 to 30% by weight based on the total amount of the organic hydroxyl compound, polyphosphoric acid and phosphorus pentaoxide used in the reaction. When the amount of water is less than 1% by weight, the hydrolysis will be poor, while when it exceeds 30% by weight, the reaction system will tend to have an increased viscosity or gel during the hydrolysis. The temperature of the hydrolysis is generally 40° to 120° C., preferably 60° to 100° C. and the reaction time is generally 1 to 24 hours, preferably 2 to 10 hours. When the temperature of the hydrolysis is lower than 40° C., the hydrolysis will be poor, while when it exceeds 120° C., the decomposition of phosphoric esters formed will tend to proceed. When the reaction time is less than one hour, the hydrolysis will be poor, while when it exceeds 24 hours, the decomposition of phosphoric monoester formed will tend to proceed.

According to the present invention, it is preferable that the reaction product which has been subjected to the hydrolysis described above or has not been subjected thereto be freed from unreacted organic hydroxyl compound. The product can be deodorized by the removal of the organic hydroxyl compound unreacted. Although the method for the removal of the unreacted organic hydroxyl compound (i.e., the method for the deodorization) is not particularly limited, examples of the methods include steam distillation, extraction and crystallization, among which steam distillation is preferable with that using a thin film being still more preferable.

The process according to the present invention makes it possible to prepare a phosphoric monoester having an extremely high purity, a lowered orthophosphoric acid content and good odor industrially easily without giving a reaction product of high-viscosity gel over all of the stages of the process.

BRIEF DESCRIPTION OF THE DRAWINGS

In FIG. 1, numerals 1, 2, 3, 4, 5, 6, 7, 8 and 9 represent the body of a steam distillator, stirring motor, feed line, distributor, scraper, steam line, residue line, distillate (vacuum) line and mantle heater, respectively.

EXAMPLES

The present invention will now be described by referring to the following Examples, though the present invention is not limited to these Examples only.

Example 1

116 wt % (calculated in orthophosphoric acid units) polyphosphoric acid (a product of Nippon Chemical Industries Co., Ltd., trade name: Polyphosphoric acid 116), 112.6 g [water: 18.0 g (1.0 mol), $P_2O_5$: 94.6 g (0.67 mol)], was added to 372.6 g (2.0 mol) of lauryl alcohol (MW: 186.3). The obtained mixture was stirred at 80° C. for 3 hours to conduct a reaction. The value of the above formula (1) was 4.5. Then, phosphorus pentaoxide (active ingredient: 98.5 wt %), 48.1 g ($P_2O_5$: 0.33 mol), was gradually added to the obtained reaction product at 80° C. and the obtained mixture was kept at that temperature for 12 hours to conduct phosphorylation. The value of the above formula (1) was 3.0. 26.6 g of deionized water was added to the obtained reaction product and the obtained mixture was kept at 80° C. for 3 hours to conduct hydrolysis. The reaction product thus obtained comprised 71.2 mole % of monolauryl phosphate, 7.9 mole % of dilauryl phosphate, 15.0 mole % of orthophosphoric acid and 5.9 mole % of unreacted alcohol, exclusive of water.

Figure 1:
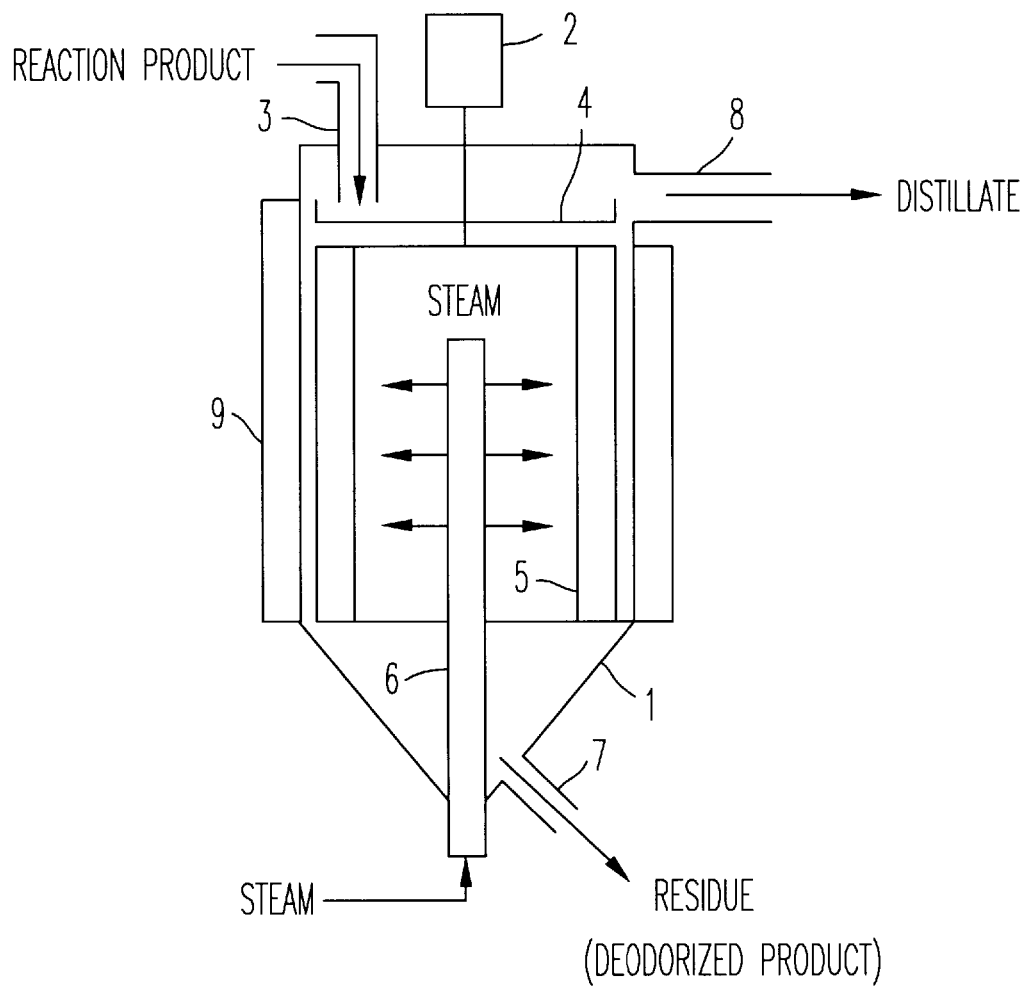
FIG. 1 is a schematic cross-sectional view of a steam distillator with forced thin film used in Examples.

Further, the reaction product was subjected to deodorization using a steam distillator (heat transfer area: 0.03 $m^2$, made of glass) with forced thin film as shown in FIG. 1. The deodorization was conducted at a temperature of the mantle heater 9 (the temperature of the outside wall of the steam distillator) of 150° C. and 20 mmHg by continuously feeding the reaction product and steam through feed line 3 and steam line 6 at rates of 100 g/hr and 150 g/hr respectively to give an objective phosphoric monoester-containing product as a residue. The distillate was a mixture comprising unreacted alcohol and water. The obtained residue comprised 75.4 mole % of monolauryl phosphate, 8.4 mole % of dilauryl phosphate, 15.9 mole % of orthophosphoric acid and 0.36 mole % of unreacted alcohol, exclusive of water.

The analysis of the reaction product (or the residue) was conducted as follows:
(Analysis for phosphoric monoester, phosphoric diester and orthophosphoric acid)

The reaction product was subjected to extraction with diethyl ether to conduct the partition of the product between the ether and water, giving an aqueous phase containing orthophosphoric acid and an organic phase containing phosphoric monoester and phosphoric diester. Each phase was subjected to potentiometric titration to determine the orthophosphoric acid content.

More specifically, about 5 g (a g) of a sample, 100 ml of 0.1N hydrochloric acid and 100 ml of diethyl ether were put in a 500-ml separatory funnel. The resulting funnel was vigorously shaken and thereafter allowed to stand, by which the contents were separated into two phases. The lower layer (aqueous phase) was subjected to potentiometric titration with an 0.5N aqueous solution of potassium hydroxide to determine the amount (b mol) of alkali consumed until the reaction reached the first equivalence point and that (c mol) thereof consumed until the reaction reached the second equivalence point. The orthophosphoric acid content was calculated according to the following formula (3):

$$\text{orthophosphoric acid content (wt \%)} = \frac{98.00 \times (c - b)}{a} \times 100. \quad (3)$$

The organic phase was distilled to remove the ether. Tetrahydrofuran was added to the residue to make up to a total amount of 100 ml. 10 ml of the resulting mixture was sampled with a transfer pipette and added to a mixture comprising 55 ml of tetrahydrofuran and 35 ml of deionized water, followed by dissolution. The obtained solution was subjected to potentiometric titration with a 0.5N aqueous solution of potassium hydroxide to determine the amount (d mol) of alkali consumed until the reaction reached the first equivalence point and that (e mol) thereof consumed until the reaction reached the second equivalence point. The phosphoric monoester content and phosphoric diester content were determined according to the following formulae (4) and (5):

$$\begin{array}{c}\text{phosphoric}\\\text{monoester}\\\text{content}\\\text{(wt \%)}\end{array} = \frac{e-d}{a} \times \left[\begin{array}{c}\text{mol. wt. of}\\\text{phosphoric}\\\text{monoester}\end{array}\right] \times 1000 \quad (4)$$

and $$\begin{array}{c}\text{phosphoric}\\\text{diester}\\\text{content}\\\text{(wt \%)}\end{array} = \frac{2d-e}{a} \times \left[\begin{array}{c}\text{mol. wt. of}\\\text{phosphoric}\\\text{diester}\end{array}\right] \times 1000. \quad (5)$$

Although the calculation according to the above formulae (3), (4) and (5) give contents in wt %, the contents in wt % are converted into those in mole % and described in Examples and Comparative Examples.

(Analysis for unreacted organic hydroxyl compound)

The analysis for unreacted organic hydroxyl compound was conducted by extraction with petroleum ether. More specifically, 5 to 10 g of a sample was dissolved in a mixture comprising 100 ml of isopropanol and 100 ml of 15% by weight aqueous solution of triethanolamine. The obtained solution was transferred to a 500-ml separatory funnel and extracted with 100 ml of petroleum ether thrice. The petroleum ether phases were combined each other and washed with 100 ml of 50% by volume aqueous solution of ethanol twice and with 100 ml of deionized water once. The resulting petroleum ether phase was dried over anhydrous sodium sulfate and then distilled to remove the petroleum ether. The resulting residue (petroleum ether extract) was dried at room temperature under a reduced pressure (about 200 mmHg) until a constant weight was reached. The weight of the petroleum ether extract was accurately determined.

Although the weight of the unreacted organic hydroxyl compound is given by the above method, the mole % is calculated from the weight thereof and described in Examples and Comparative Examples.

Comparative Example 1

Phosphorus pentaoxide (active ingredient: 98.5 wt %), 48.1 g ($P_2O_5$: 0.33 mol), was gradually added to 372.6 g (2.0 mol) of lauryl alcohol (MW: 186.3) and the obtained mixture was stirred at 80° C. for 3 hours to conduct phosphorylation. The value of the above formula (1) (wherein the "polyphosphoric acid" in the numerator is replaced by "phosphorus pentaoxide") was 6.0. 116 wt % (calculated in orthophosphoric acid units) polyphosphoric acid (a product of Nippon Chemical Industries Co., Ltd., trade name: Polyphosphoric acid 116), 112.6 g [water: 18.0 g (1.0 mol), $P_2O_5$: 94.6 g (0.67 mol)], was added to the obtained reaction product at 80° C. and the obtained mixture was kept at that temperature for 12 hours to conduct phosphorylation. The value of the above formula (1) was 3.0. 26.6 g of deionized water was added to the obtained reaction product and the obtained mixture was kept at 80° C. for 3 hours to conduct hydrolysis. The reaction product thus obtained comprised 65.7 mole % of monolauryl phosphate, 11.9 mole % of dilauryl phosphate, 17.0 mole % of orthophosphoric acid and 5.4 mole % of unreacted alcohol, exclusive of water.

Further, the reaction product was subjected to deodorization in the same manner as that of Example 1 under the same conditions as those of Example 1 to give an objective phosphoric monoester-containing product as a residue. This residue comprised 69.2 mole % of monolauryl phosphate, 12.5 mole % of dilauryl phosphate, 17.9 mole % of orthophosphoric acid and 0.36 mole % of unreacted alcohol, exclusive of water.

Comparative Example 2

116 wt % (calculated in orthophosphoric acid units) polyphosphoric acid (a product of Nippon Chemical Industries Co., Ltd., trade name: Polyphosphoric acid 116), 112.6 g [water: 18.0 g (1.0 mol), $P_2O_5$: 94.6 g (0.67 mol)], was added to 372.6 g (2.0 mol) of lauryl alcohol (MW: 186.3). The obtained mixture was stirred at 80° C. for 3 hours to conduct a reaction. The value of the above formula (1) was 4.5. Then, phosphorus pentaoxide (active ingredient: 98.5 wt %), 76.9 g ($P_2O_5$: 0.53 ml), was gradually added to the reaction product thus obtained at 80° C. and the obtained mixture was kept at that temperature for 6 hours to conduct phosphorylation. The value of the above formula (1) was 2.5. 26.6 g of deionized water was added to the obtained reaction product and the obtained mixture was kept at 80° C. for 3 hours to conduct hydrolysis. The reaction product thus obtained comprised 60.6 mole % of monolauryl phosphate, 6.8 mole % of dilauryl phosphate, 28.0 mole % of orthophosphoric acid and 4.6 mole % of unreacted alcohol, exclusive of water.

Further, the reaction product was subjected to deodorization in the same manner as that of Example 1 under the same conditions as those of Example 1 to give an objective phosphoric monoester-containing product as a residue. This residue comprised 63.3 mole % of monolauryl phosphate, 7.1 mole % of dilauryl phosphate, 29.3 mole % of orthophosphoric acid and 0.30 mole % of unreacted alcohol, exclusive of water.

Example 2

1.5 g of 75 wt % (calculated in orthophosphoric acid units) phosphoric acid was added to 85.8 g of 116 wt % (calculated in orthophosphoric acid units) polyphosphoric acid (a product of Nippon Chemical Industries Co., Ltd., trade name: Polyphosphoric acid 116). The obtained mixture was stirred at 80° C. for 5 hours to give a homogeneous polyphosphoric acid having a concentration of 115 wt % (calculated in orthophosphoric acid units).

This 115 wt % polyphosphoric acid, 87.3 g [water: 14.4 g (0.8 mol), $P_2O_5$: 72.9 g (0.51 mol)], was added to 595.1 g (2.2 mol) of stearyl alcohol (MW: 270.5). The obtained mixture was stirred at 80° C. for 2 hours to conduct a reaction. The value of the above formula (1) was 5.9. Then, phosphorus pentaoxide (active ingredient: 98.5 wt %), 70.1 g ($P_2O_5$: 0.49 mol), was gradually added to the obtained reaction product at 80° C. and the obtained mixture was kept at that temperature for 12 hours to conduct phosphorylation. The value of the above formula (1) was 3.0. 37.6 g of deionized water was added to the reaction product thus obtained and the obtained mixture was kept at 80° C. for 3 hours to conduct hydrolysis. The reaction product thus obtained comprised 73.0 mole % of monostearyl phosphate, 12.3 mole % of distearyl phosphate, 9.0 mole % of orthophosphoric acid and 5.7 mole % of unreacted alcohol, exclusive of water.

Further, the reaction product was subjected to deodorization in the same manner as that of Example 1 under the same conditions as those of Example 1 to give an objective phosphoric monoester-containing product as a residue. The residue comprised 75.6 mole % of monostearyl phosphate, 12.7 mole % of distearyl phosphate, 9.3 mole % of orthophosphoric acid and 2.4 mole % of unreacted alcohol, exclusive of water.

Comparative Example 3

75 wt % (calculated in orthophosphoric acid units) phosphoric acid, 31.5 g [water: 14.4 g (0.8 mol), $P_2O_5$: 17.1 g (0.12 mol)], was added to 595.1 g (2.2 mol) of stearyl alcohol (MW: 270.5). The obtained mixture was stirred at 80° C. for 2 hours to conduct a reaction. The value of the above formula (1) (wherein the "polyphosphoric acid" in the numerator is replaced by "phosphoric acid") was 25.0. Phosphorus pentaoxide (active ingredient: 98.5 wt %), 126.7 g ($P_2O_5$: 0.88 mol), was gradually added to the obtained reaction product at 80° C. and the obtained mixture was kept at that temperature for 12 hours to conduct phosphorylation. The value of the above formula (1) (wherein the "polyphosphoric acid" in the numerator is replaced by "phosphoric acid") was 3.0. 37.6 g of deionized water was added to the obtained reaction product and the obtained mixture was kept at 80° C. for 3 hours to conduct hydrolysis. The reaction product thus obtained comprised 70.4 mole % of monostearyl phosphate, 15.2 mole % of distearyl phosphate, 10.0 mole % of orthophosphoric acid and 4.4 mole % of unreacted alcohol, exclusive of water.

Further, the reaction product was subjected to deodorization in the same manner as that of Example 1 under the same conditions as those of Example 1 to give an objective phosphoric monoester-containing product as a residue. This residue comprised 71.9 mole % of monostearyl phosphate, 15.5 mole % of distearyl phosphate, 10.2 mole % of orthophosphoric acid and 2.3 mole % of unreacted alcohol, exclusive of water.

Comparative Example 4

An attempt was made to prepare a polyphosphoric acid having a concentration of 125 wt % (calculated in orthophosphoric acid units) for the purpose of preparing a mixture having a value of the above formula (1) of 3.0 by adding 156.3 g of this polyphosphoric acid [water: 14.4 g (0.8 mol), $P_2O_5$: 141.9 g (1.0 mol)] to 595.1 g (2.2 mol) of stearyl alcohol (MW: 270.5). Namely, phosphorus pentaoxide (active ingredient: 98.5 wt %), 144.1 g ($P_2O_5$: 1.00 mol), was gradually added to 14.4 g of water at 80° C. In the course of this addition, the mixture became highly viscous, so that after the completion of the addition, the obtained mixture (phosphorylating agent) was stirred at 90° C. for 24 hours. However, the resulting mixture was still unhomogeneous and highly viscous, so that it could not be added to stearyl alcohol.

Example 3

8.7 g of 75 wt % (calculated in orthophosphoric acid units) phosphoric acid was added to 110.3 g of 116 wt % (calculated in orthophosphoric acid units) polyphosphoric acid (a product of Nippon Chemical Industries Co., Ltd., trade name: Polyphosphoric acid 116). The obtained mixture was stirred at 90° C. for 5 hours to give a homogeneous polyphosphoric acid having a phosphoric acid concentration of 113 wt % (calculated in orthophosphoric acid units).

This 113 wt % polyphosphoric acid, 119.0 g [water: 21.6 g (1.2 mol), $P_2O_5$: 97.4 g (0.69 mol)] was added to 335.3 g (1.8 mol) of lauryl alcohol (MW: 186.3). The obtained mixture was stirred at 80° C. for 5 hours to conduct a reaction. The value of the above formula (1) was 4.3. Then, phosphorus pentaoxide (active ingredient: 98.5 wt %), 45.2 g ($P_2O_5$: 0.31 mol), was gradually added to the obtained reaction product at 80° C. and the obtained mixture was kept at that temperature for 12 hours to conduct phosphorylation. The value of the formula (1) was 3.0. 25.0 g of deionized water was added to the reaction product and the obtained mixture was kept at 80° C. for 3 hours to conduct hydrolysis. The reaction product thus obtained comprised 69.7 mole % of monolauryl phosphate, 5.0 mole % of dilauryl phosphate, 19.9 mole % of orthophosphoric acid and 5.4 mole % of unreacted alcohol, exclusive of water.

Further, the reaction product was subjected to deodorization in the same manner as that of Example 1 under the same conditions as those of Example 1 to give an objective phosphoric monoester-containing product as a residue. This residue comprised 73.4 mole % of monolauryl phosphate, 5.3 mole % of dilauryl phosphate, 21.0 mole % of orthophosphoric acid and 0.33 mole % of unreacted alcohol, exclusive of water.

Comparative Example 5

21.6 g of water (1.2 mol) was added to 167.7 g (0.90 mol) of lauryl alcohol (MW: 186.3). The obtained mixture was stirred at 50° C. for 0.5 hour. Then, phosphorus pentaoxide (active ingredient: 98.5%), 144.1 g ($P_2O_5$: 1.0 mol), was gradually added to the resulting mixture at 80° C. and the obtained mixture was kept at that temperature for 2 hours to conduct phosphorylation. The value of the above formula (1) (wherein the "molar amount of water included in the polyphosphoric acid represented as $P_2O_5 \cdot nH_2O$" in the numerator is replaced by "Molar amount of water") was 2.1. Then, 167.7 g (0.90 mol) of lauryl alcohol was added to the obtained reaction product at 80° C. and the obtained mixture was kept at that temperature for 12 hours to conduct phosphorylation. The value of the above formula (1) (wherein the "molar amount of water included in the polyphosphoric acid represented as $P_2O_5 \cdot nH_2O$" in the numerator is replaced by "Molar amount of water") was 3.0. 25.0 g of deionized water was added to the obtained reaction product and the obtained mixture was kept at 80° C. for 3 hours to conduct hydrolysis. The reaction product thus obtained comprised 67.6 mole % of monolauryl phosphate, 6.6 mole % of dilauryl phosphate, 20.9 mole % of orthophosphoric acid and 4.9 mole % of unreacted alcohol, exclusive of water.

Further, the reaction product was subjected to deodorization in the same manner as that of Example 1 under the same conditions as those of Example 1 to give an objective phosphoric monoester-containing product as a residue. This residue comprised 70.8 mole % of monolauryl phosphate, 6.9 mole % of dilauryl phosphate, 21.9 mole % of orthophosphoric acid and 0.33 mole % of unreacted alcohol, exclusive of water.

Example 4

116 wt % (calculated in orthophosphoric acid units) polyphosphoric acid (a product of Nippon Chemical Industries Co., Ltd., trade name: Polyphosphoric acid 116), 112.6 g [water: 18.0 g (1.0 mol), $P_2O_5$: 94.6 g (0.67 mol)], was added to 861.6 g (2.0 mol) of polyoxyethylene nonylphenyl ether (a product of Kao Corporation, trade name: Emulgen 905, MW: 430.8, average number of EO molecules added: 4.7). The obtained mixture was stirred at 90° C. for one hour to conduct a reaction. The value of the above formula (1) was 4.5. Then, phosphorus pentaoxide (active ingredient: 98.5 wt %), 48.1 g ($P_2O_5$: 0.33 mol), was gradually added to the reaction product at 90° C. and the obtained mixture was kept at that temperature for 8 hours to conduct phosphorylation. The value of the above formula (1) was 3.0. 35.5 g of deionized water was added to the obtained reaction product and the obtained mixture was kept at 80° C. for 5 hours to conduct hydrolysis. The reaction product thus obtained comprised 71.0 mole % of phosphoric monoester, 8.2 mole % of phosphoric diester, 14.8 mole % of orthophosphoric acid and 6.0 mole % of unreacted organic hydroxyl compound, exclusive of water.

Example 5

The same procedure as that of Example 1 was repeated up to the hydrolysis step, except that 345.7 g (2.0 mol) of Neodol 1 (a product of Shell, saturated aliphatic alcohols having 11 carbon atoms, MW: 172.9, linear alcohol: 82 mole %, methyl-branched alcohol: 18 mole %) was used as the organic hydroxyl compound. The reaction product thus obtained comprised 71.3 mole % of phosphoric monoester, 7.8 mole % of phosphoric diester, 14.9 mole % of orthophosphoric acid and 6.5 mole % of unreacted organic hydroxyl compound, exclusive of water.

Further, the reaction product was subjected to deodorization in the same manner as that of Example 1 under the same conditions as those of Example 1 to give an objective phosphoric monoester-containing product as a residue. This residue comprised 75.7 mole % of phosphoric monoester, 8.3 mole % of phosphoric diester, 15.7 mole % of orthophosphoric acid and 0.30 mole % of unreactred alcohol, exclusive of water.

Example 6

27.2 g of 116 wt % (calculated in orthophosphoric acid units) polyphosphoric acid (a product of Nippon Chemical Industries Co., Ltd., trade name: Polyphosphoric acid 116) was mixed with 2.3 g of 75 wt % (calculated in orthophosphoric acid units) phosphoric acid at 80° C. by stirring for 5 hours to give a homogeneous polyphosphoric acid having a phosphoric acid concentration of 112.8 wt % (calculated in orthophosphoric acid units).

This 112.8 wt % polyphosphoric acid, 29.5 g [water: 5.4 g (0.3 mol), $P_2O_5$: 24.1 g (0.17 mol)], was added to 503.0 g (2.7 mol) of lauryl alcohol (MW: 186.3). The obtained mixture was stirred at 80° C. for 2 hours to conduct a reaction. The value of the above formula (1) was 17.6. Then, phosphorus pentaoxide (active ingredient: 98.5 wt %), 119.6 g ($P_2O_5$: 0.83 mol), was gradually added to the obtained reaction product at 80° C. and the obtained mixture was kept at that temperature for 12 hours to conduct phosphorylation. The value of the above formula (1) was 3.0. 47.0 g of deionized water was added to the obtained reaction product and the resulting mixture was kept at 80° C. for 3 hours to conduct hydrolysis. The reaction product thus obtained comprised 55.3 mole % of monolauryl phosphate, 30.4 mole % of dilauryl phosphate, 6.3 mole % of orthophosphoric acid and 8.0 mole % of unreacted alcohol, exclusive of water.

Further, the reaction product was subjected to deodorization in the same manner as that of Example 1 under the same conditions as those of Example 1 to give an objective phosphoric monoester-containing product as a residue. This residue comprised 59.8 mole % of monolauryl phosphate, 33.0 mole % of dilauryl phosphate, 6.8 mole. % of orthophosphoric acid and 0.35 mole % of unreacted alcohol, exclusive of water.

Example 7

38.2 g of 116 wt % (calculated in orthophosphoric acid units) polyphosphoric acid (a product of Nippon Chemical Industries Co., Ltd., trade name: Polyphosphoric acid 116) was mixed with 6.3 g of 75 wt % (calculated in orthophosphoric acid units) phosphoric acid at 80° C. by stirring for 5 hours to give a homogeneous polyphosphoric acid having a phosphoric acid concentration of 110.1 wt % (calculated in orthophosphoric acid units).

This 110.1 wt % polyphosphoric acid, 44.5 g [water: 9.0 g (0.5 mol), $P_2O_5$: 35.5 g (0.25 mol)], was added to 465.8 g (2.5 mol) of lauryl alcohol (MW: 186.3). The obtained mixture was stirred at 70° C. for 3 hours to conduct a reaction. The value of the above formula (1) was 12.0. Then, phosphorus pentaoxide (active ingredient: 98.5 wt %), 108.1 g ($P_2O_5$: 0.75 mol), was gradually added to the obtained reaction product at 70° C. and the obtained mixture was kept at 90° C. for 8 hours to conduct phosphorylation. The value of the above formula (1) was 3.0. 35.0 g of deionized water was added to the obtained reaction product and the resulting mixture was kept at 80° C. for 3 hours to conduct hydrolysis. The reaction product thus obtained comprised 63.5 mole % of monolauryl phosphate, 23.2 mole % of dilauryl phosphate, 6.6 mole % of orthophosphoric acid and 6.7 mole % of unreacted alcohol, exclusive of water.

Further, the reaction product was subjected to deodorization in the same manner as that of Example 1 under the same conditions as those of Example 1 to give an objective phosphoric monoester-containing product as a residue. This residue comprised 67.8 mole % of monolauryl phosphate, 24.8 mole % of dilauryl phosphate, 7.1 mole % of orthophosphoric acid and 0.30 mole % of unreacted alcohol, exclusive of water.

Example 8

2.4 g of phosphorus pentaoxide (active ingredient: 98.5 wt %) was added to 56.3 g of 116 wt % (calculated in orthophosphoric acid units) polyphosphoric acid (a product of Nippon Chemical Industries Co., Ltd., trade name: Polyphosphoric acid 116). The obtained mixture was stirred at 90° C. for 8 hours to give a homogeneous polyphosphoric acid having a phosphoric acid concentration of 116.9 wt % (calculated in orthophosphoric acid units).

This 116.9 wt % polyphosphoric acid, 58.7 g [water: 9.0 g (0.5 mol), $P_2O_5$: 49.7 g (0.35 mol)], was added to 465.8 g (2.5 mol) of lauryl alcohol (MW: 186.3). The obtained mixture was stirred at 70° C. for 3 hours to conduct a reaction. The value of the above formula (1) was 8.6. Then, phosphorus pentaoxide (active ingredient: 98.5 wt %), 93.7 g ($P_2O_5$: 0.65 mol), was gradually added to the obtained reaction product at 70° C. and the obtained mixture was kept at 90° C. for 8 hours to conduct phosphorylation. The value of the above formula (1) was 3.0. 35.0 g of deionized water was added to the obtained reaction product and the resulting mixture was kept at 80° C. for 3 hours to conduct hydrolysis. The reaction product thus obtained comprised 64.7 mole % of monolauryl phosphate, 22.4 mole % of dilauryl phosphate, 6.0 mole % of orthophosphoric acid and 6.6 mole % of unreacted alcohol, exclusive of water.

Further, the reaction product was subjected to deodorization in the same manner as that of Example 1 under the same conditions as those of Example 1 to give an objective phosphoric monoester-containing product as a residue. This residue comprised 69.1 mole % of monolauryl phosphate, 24.2 mole % of dilauryl phosphate, 6.4 mole % of orthophosphoric acid and 0.30 mole % of unreacted alcohol, exclusive of water.

Example 9

17.8 g of phosphorus pentaoxide (active ingredient: 98.5 wt %) was added to 112.6 g of 116 wt % (calculated in orthophosphoric acid units) polyphosphoric acid (a product of Nippon Chemical Industries Co., Ltd., trade name: Polyphosphoric acid 116). The obtained mixture was stirred at 90° C. for 8 hours to give a homogeneous polyphosphoric acid having a phosphoric acid concentration of 118.7 wt % (calculated in orthophosphoric acid units).

This 118.7 wt % polyphosphoric acid, 130.4 g [water: 18.0 g (1.0 mol), $P_2O_5$: 112.1 g (0.79 mol), the other components: 0.3 g], was added to 372.6 g (2.0 mol) of lauryl alcohol (MW: 186.3). The obtained mixture was stirred at 70° C. for 3 hours to conduct a reaction. The value of the above formula (1) was 3.8. Then, phosphorus pentaoxide (active ingredient: 98.5 wt %), 30.3 g ($P_2O_5$: 0.21 mol), was gradually added to the obtained reaction product at 70° C. and the obtained mixture was kept at 90° C. for 8 hours to conduct a phosphorylation. The value of the above formula (1) was 3.0. 26.5 g of deionized water was added to the obtained reaction product and the resulting mixture was kept at 80° C. for 3 hours to conduct hydrolysis. The reaction product thus obtained comprised 71.2 mole % of monolauryl phosphate, 8.3 mole % of dilauryl phosphate, 14.5 mole % of orthophosphoric acid and 6.0 mole % of unreacted alcohol, exclusive of water.

Further, the reaction product was subjected to deodorization in the same manner as that of Example 1 under the same conditions as those of Example 1 to give an objective phosphoric monoester-containing product as a residue. This residue comprised 75.5 mole % of monolauryl phosphate, 8.8 mole % of dilauryl phosphate, 15.4 mole % of orthophosphoric acid and 0.27 mole % of unreacted alcohol, exclusive of water.

Example 10

116 wt % (calculated in orthophosphoric acid units) polyphosphoric acid (a product of Nippon Chemical Industries Co., Ltd., trade name: Polyphosphoric acid 116), 112.6 g [water: 18.0 g (1.0 mol), $P_2O_5$: 94.6 g (0.67 mol)], was added to 372.6 g (2.0 mol) of lauryl alcohol (MW: 186.3). The obtained mixture was stirred at 80° C. for 3 hours to conduct a reaction. The value of the above formula (1) was 4.5. Then, phosphorus pentaoxide (active ingredient: 98.5 wt %), 55.6 g ($P_2O_5$: 0.39 mol), was gradually added to the obtained reaction product at 80° C. and the obtained mixture was kept at that temperature for 8 hours to conduct phosphorylation. The value of the above formula (1) was 2.85. 30.2 g of deionized water was added to the obtained reaction product and the resulting mixture was kept at 80° C. for 3 hours to conduct hydrolysis. The reaction product thus obtained comprised 69.5 mole % of monolauryl phosphate, 8.2 mole % of dilauryl phosphate, 17 6 mole % of orthophosphoric acid and 4.7 mole % of unreacted alcohol, exclusive of water.

Further, the reaction product was subjected to deodorization in the same manner as that of Example 1 under the same conditions as those of Example 1 to give an objective phosphoric monoester-containing product as a residue. This residue comprised 72.7 mole % of monolauryl phosphate, 8.6 mole % of dilauryl phosphate, 18.4 mole % of orthophosphoric acid and 0.30 mole % of unreacted alcohol, exclusive of water.

Example 11

116 wt % (calculated in orthophosphoric acid units) polyphosphoric acid (a product of Nippon Chemical Industries Co., Ltd., trade name: Polyphosphoric acid 116), 112.6 g [water: 18.0 g (1.0 mol), $P_2O_5$: 94.6 g (0.67 mol)], was added to 372.6 g (2.0 mol) of lauryl alcohol (MW: 186.3). The obtained mixture was stirred at 80° C. for 3 hours to conduct a reaction. The value of the above formula (1) was 4.5. Then, phosphorus pentaoxide (active ingredient: 98.5 wt%), 50.5 g ($P_2O_5$: 0.35 mol), was gradually added to the obtained reaction product at 80° C. and the obtained mixture was kept at that temperature for 10 hours to conduct phosphorylation. The value of the above formula (1) was 2.95. 28.2 g of deionized water was added to the obtained reaction product and the resulting mixture was kept at 80° C. for 3 hours to conduct hydrolysis. The reaction product thus obtained comprised 72.5 mole % of monolauryl phosphate, 8.2 mole % of dilauryl phosphate, 14.5 mole % of orthophosphoric acid and 4.7 mole % of unreacted alcohol, exclusive of water.

Further, the reaction product was subjected to deodorization in the same manner as that of Example 1 under the same conditions as those of Example 1 to give an objective phosphoric monoester-containing product as a residue. This residue comprised 75.8 mole % of monolauryl phosphate, 8.6 mole % of dilauryl phosphate, 15.3 mole % of orthophosphoric acid and 0.31 mole % of unreacted alcohol, exclusive of water.

Example 12

116 wt % (calculated in orthophosphoric acid units) polyphosphoric acid (a product of Nippon Chemical Industries Co.; Ltd., trade name: Polyphosphoric acid 116), 112.6 g [water: 18.0 g (1.0 mol), $P_2O_5$: 94.6 g (0.67 mol)], was added to 372.6 g (2.0 mol) of lauryl alcohol (MW: 186.3). The obtained mixture was stirred at 80° C. for 3 hours to conduct a reaction. The value of the above formula (1) was 4.5. Then, phosphorus pentaoxide (active ingredient: 98.5 wt %), 45.7 g ($P_2O_5$: 0.32 mol), was gradually added to the obtained reaction product at 80° C. and the obtained mixture was kept at that temperature for 12 hours to conduct phosphorylation. The value of the above formula (1) was 3.05. 25.2 g of deionized water was added to the obtained reaction product and the resulting mixture was kept at 80° C. for 3 hours to conduct hydrolysis. The reaction product thus obtained comprised 70.0 mole % of monolauryl phosphate, 7.3 mole % of dilauryl phosphate, 14.2 mole % of orthophosphoric acid and 8.4 mole % of unreacted alcohol, exclusive of water.

Further, the reaction product was subjected to deodorization in the same manner as that of Example 1 under the same conditions as those of Example 1 to give an objective phosphoric monoester-containing product as a residue. This residue was comprised 76.1 mole % of monolauryl phosphate, 7.9 mole % of dilauryl phosphate, 15.5 mole % of orthophosphoric acid and 0.43 mole % of unreacted alcohol, exclusive of water.

Example 13

116 wt % (calculated in orthophosphoric acid units) polyphosphoric acid (a product of Nippon Chemical Industries Co., Ltd., trade name: Polyphosphoric acid 116), 112.6 g [water: 18.0 g (1.0 mol), $P_2O_5$: 94.6 g (0.67 mol)], was added to 372.6 g (2.0 mol) of lauryl alcohol (MW: 186.3). The obtained mixture was stirred at 80° C. for 3 hours to conduct a reaction. The value of the above formula (1) was 4.5. Then, phosphorus pentaoxide (active ingredient: 98.5 wt %), 41.2 g ($P_2O_5$: 0.29 mol), was gradually added to the obtained reaction product at 80° C. and the obtained mixture was kept at that temperature for 12 hours to conduct phosphorylation. The value of the above formula (1) was 3.15.

25.2 g of deionized water was added to the obtained reaction product and the resulting mixture was kept at 80° C. for 3 hours to conduct hydrolysis. The reaction product thus obtained comprised 66.7 mole % of monolauryl phosphate, 6.7 mole % of dilauryl phosphate, 14.5 mole % of orthophosphoric acid and 12.1 mole % of unreacted alcohol, exclusive of water.

Further, the reaction product was subjected to deodorization in the same manner as that of Example 1 under the same conditions as those of Example 1 to give an objective phosphoric monoester-containing product as a residue. This residue comprised 75.5 mole % of monolauryl phosphate, 7.6 mole % of dilauryl phosphate, 16.4 mole % of orthophosphoric acid and 0.55 mole % of unreacted alcohol, exclusive of water.

Comparative Example 6

116 wt % (calculated in orthophosphoric acid units) polyphosphoric acid (a product of Nippon Chemical Industries Co., Ltd., trade name: Polyphosphoric acid 116), 112.6 g [water: 18.0 g (1.0 mol), $P_2O_5$: 94.6 g (0.67 mol)], was added to 372.6 g (2.0 mol) of lauryl alcohol (MW: 186.3). The obtained mixture was stirred at 80° C. for 3 hours to conduct a reaction. The value of the above formula (1) was 4.5. Then, phosphorus pentaoxide (active ingredient: 98.5 wt %), 27.5 g ($P_2O_5$: 0.19 mol), was gradually added to the obtained reaction product at 80° C. and the obtained mixture was kept at that temperature for 12 hours to conduct phosphorylation. The value of the above formula (1) was 3.5. 25.2 g of deionized water was added to the obtained reaction product and the resulting mixture was kept at 80° C. for 3 hours to conduct hydrolysis. The reaction product thus obtained comprised 56.3 mole % of monolauryl phosphate, 4.6 mole % of dilauryl phosphate, 15.5 mole % of orthophosphoric acid and 23.7 mole % of unreacted alcohol, exclusive of water.

Further, the reaction product was subjected to deodorization in the same manner as that of Example 1 under the same conditions as those of Example 1 to give an objective phosphoric monoester-containing product as a residue. This residue comprised 72.8 mole % of monolauryl phosphate, 5.9 mole % of dilauryl phosphate, 20.0 mole % of orthophosphoric acid and 1.35 mole % of unreacted alcohol, exclusive of water.

The purity for a phosphoric monoester and orthophosphoric rate (which are based on phosphoric esters) were calculated by the following formulae (6) and (7) respectively with respect to the reaction products of Examples 1 to 13 and Comparative Examples 1 to 6:

$$\text{purity for a phosphoric monoester (mole \%)} = \frac{\text{phosphoric monoester (mole \%)}}{\left(\begin{array}{c}\text{phosphoric}\\\text{monoester}\\\text{(mole \%)}\end{array}\right) + \left(\begin{array}{c}\text{phosphoric}\\\text{diester}\\\text{(mole \%)}\end{array}\right)} \times 100 \quad (6)$$

and $$\text{ortho-phosphoric acid rate (mole \%)} = \frac{\text{orthophosphoric acid (mole \%)}}{\left(\begin{array}{c}\text{phosphoric}\\\text{monoester}\\\text{(mole \%)}\end{array}\right) + \left(\begin{array}{c}\text{phosphoric}\\\text{diester}\\\text{(mole \%)}\end{array}\right)} \times 100. \quad (7)$$

Figure 2:
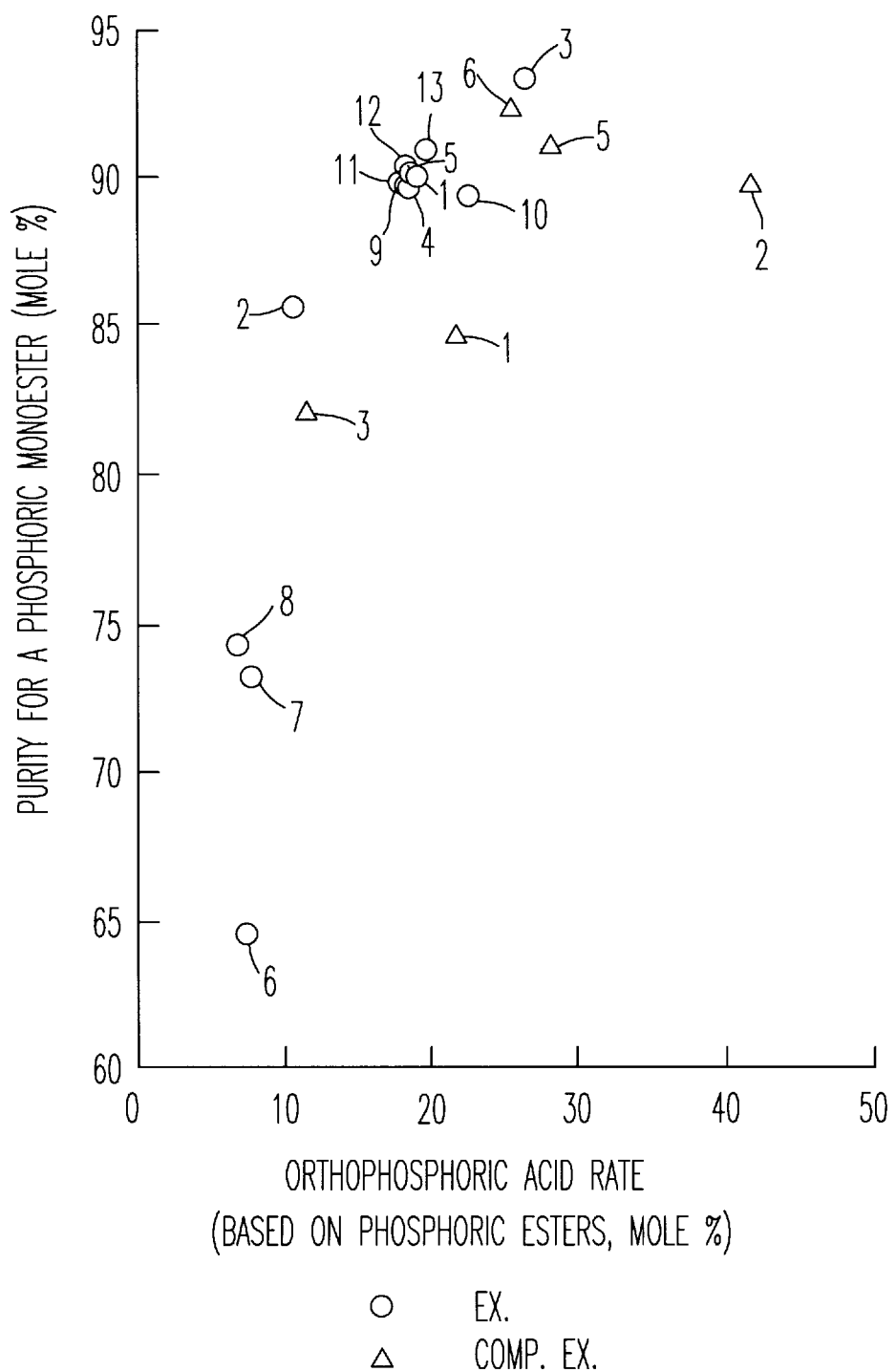
FIG. 2 is a graph wherein the results of analysis of the reaction products of Examples 1 to 13 and Comparative Examples 1 to 3, 6 and 7 are plotted with purity for a phosphoric monoester as ordinate and orthophosphoric acid rate as abscissa.

The results are given in Table 1. Further, FIG. 2 shows a graph wherein the results are plotted with purity for a phosphoric monoester as ordinate and orthophosphoric acid rate as abscissa.

Furthermore, the conversion of organic hydroxyl compound was calculated by the following formula (8):

$$\text{conversion of organic hydroxyl compound (\%)} = \left[1 - \frac{\text{unreacted organic hydroxyl compound (mole \%)}}{\left(\begin{array}{c}\text{phosphoric}\\\text{monoester}\\\text{(mole \%)}\end{array}\right) + \left(\begin{array}{c}\text{phosphoric}\\\text{diester}\\\text{(mole \%)}\end{array}\right) \times 2 + \left(\begin{array}{c}\text{unreacted organic}\\\text{hydroxyl compound}\\\text{(mole \%)}\end{array}\right)}\right] \times 100. \quad (8)$$

The results are given in Table 1.

In addition, the deodorized products were evaluated for odor organoleptically. The results are also given in Table 1.

TABLE 1

| | Kind of organic hydroxyl compound | Molar ratio of fed compounds organic hydroxyl compound/ water/$P_2O_5$ | Value of formula (1) in the first step | Value of formula (1) in the second step | Purity for a phosphoric monoester (monoester / (monoester + diester)) (reaction product) (mole %) | orthophosphoric acid rate (orthophosphoric acid / (monoester + diester)) (reaction product) (based on phosphoric esters. mole %) | Conversion of organic hydroxyl compound (%) | Odor of deodorized products |
|---|---|---|---|---|---|---|---|---|
| Ex. 1 | lauryl alcohol | 2/1/1 | 4.5 | 3.0 | 90.0 | 19.0 | 93.6 | good |
| Comp. Ex. 1 | lauryl alcohol | 2/1/1 | 6.0 | 3.0 | 84.7 | 21.9 | 94.3 | nasty |
| Comp. Ex. 2 | lauryl alcohol | 2/1/1.2 | 4.5 | 2.5 | 89.9 | 41.5 | 94.2 | nasty |
| Ex. 2 | stearyl alcohol | 2.2/0.8/1 | 5.9 | 3.0 | 85.6 | 10.6 | 94.5 | good |
| Comp. Ex. 3 | stearyl alcohol | 2.2/0.8/1 | 25.0 | 3.0 | 82.2 | 11.7 | 95.8 | nasty |
| Comp. Ex. 4 | stearyl alcohol | 2.2/0.8/1 | 3.0 | — | unusable in the reaction | unusable in the reaction | unusable in the reaction | — |
| Ex. 3 | lauryl alcohol | 1.8/1.2/1 | 4.3 | 3.0 | 93.3 | 26.6 | 93.7 | good |

TABLE 1-continued

|  | Kind of organic hydroxyl compound | Molar ratio of fed compounds organic hydroxyl compound/ water/$P_2O_5$ | Value of formula (1) in the first step | Value of formula (1) in the second step | Purity for a phosphoric monoester $\left(\dfrac{\text{monoester}}{\text{monoester + diester}}\right)$ (reaction product) (mole %) | orthophosphoric acid rate $\left(\dfrac{\text{orthophosphoric acid}}{\text{monoester + diester}}\right)$ (reaction product) (based on phosphoric esters. mole %) | Conversion of organic hydroxyl compound (%) | Odor of deodorized products |
|---|---|---|---|---|---|---|---|---|
| Comp. Ex. 5 | lauryl alcohol | 1.8/1.2/1 | 2.1 | 3.0 | 91.1 | 28.2 | 94.3 | nasty |
| Ex. 4 | polyoxyethylene nonylphenyl ether | 2/1/1 | 4.5 | 3.0 | 89.6 | 18.7 | 93.6 | — |
| Ex. 5 | Neodol 1 | 2/1/1 | 4.5 | 3.0 | 90.1 | 18.8 | 93.0 | good |
| Ex. 6 | lauryl alcohol | 2.7/0.3/1 | 17.6 | 3.0 | 64.5 | 7.4 | 93.6 | good |
| Ex. 7 | lauryl alcohol | 2.5/0.5/1 | 12.0 | 3.0 | 73.2 | 7.6 | 94.3 | good |
| Ex. 8 | lauryl alcohol | 2.5/0.5/1 | 8.6 | 3.0 | 74.3 | 6.9 | 94.3 | good |
| Ex. 9 | lauryl alcohol | 2/1/1 | 3.8 | 3.0 | 89.6 | 18.2 | 93.6 | good |
| Ex. 10 | lauryl alcohol | 2/1/1.05 | 4.5 | 2.85 | 89.4 | 22.7 | 94.8 | good |
| Ex. 11 | lauryl alcohol | 2/1/1.02 | 4.5 | 2.95 | 89.8 | 18.0 | 95.0 | good |
| Ex. 12 | lauryl alcohol | 2/1/0.984 | 4.5 | 3.05 | 90.6 | 18.4 | 91.0 | good |
| Ex. 13 | lauryl alcohol | 2/1/0.952 | 4.5 | 3.15 | 90.9 | 19.8 | 86.9 | good |
| Comp. Ex. 6 | lauryl alcohol | 2/1/0.857 | 4.5 | 3.5 | 92.4 | 25.5 | 73.4 | alcoholic |

The synthesis of a phosphoric ester has a characteristic that increase in the ratio of water to an organic hydroxyl compound enhances the phosphoric monoester purity, while it also enhances the orthophosphoric acid rate.

As shown in Table 1 and FIG. 2, however, the purity of the product of Example for phosphoric monoester is higher than that of the product of Comparative Example therefor, when the orthophosphoric acid rates of both products are the same. Further, the orthophosphoric acid rate of the product of Example is lower than that of Comparative Example, when the purities of both products for phosphoric monoester are the same. Furthermore, the deodorized products of Examples are superior to those of Comparative Examples also in respect of odor.

Accordingly, it can also be understood from the results that the present invention makes it possible to prepare a high-purity phosphoric monoester having a lowered orthophosphoric acid rate and good odor.

We claim:

1. A process for the preparation of a phosphoric monoester reaction product by reacting an organic hydroxyl compound with phosphorus pentaoxide and polyphosphoric acid as phosphorylating agents, comprising:

(1) reacting an organic hydroxyl compound with polyphosphoric acid under such conditions that the ratio, as defined by formula (1), has a value exceeding 3.2, (2) adding phosphorus pentaoxide in such an amount that the ratio, as defined by formula (1), has a value in the range of from 2.8 to 3.2, and (3) removing the organic hydroxyl compound unreacted from the reaction product:

$$\frac{\left(\begin{array}{c}\text{Molar amount of water}\\ \text{included in the}\\ \text{polyphosphoric acid}\\ \text{represented as}P_2O_5\cdot nH_2O\end{array}\right) + \left(\begin{array}{c}\text{Molar amount of}\\ \text{organic hydroxyl}\\ \text{compound}\end{array}\right)}{\left(\begin{array}{c}\text{Molar amount of phosphorylating}\\ \text{agent(s) represented as } P_2O_5\end{array}\right)} \qquad (1)$$

2. The process according to claim 1, wherein the removal of the organic hydroxyl compound unreacted is conducted by steam distillation.

* * * * *

UNITED STATES PATENT AND TRADEMARK OFFICE
CERTIFICATE OF CORRECTION

PATENT NO. : 5,883,280
DATED : March 16, 1999
INVENTOR(S) : Shinji TSUYUTANI, et al.

It is certified that error appears in the above-identified patent and that said Letters Patent is hereby corrected as shown below:

On the Title page, item [87], the PCT Pub. Date should be:

--[87]
    PCT Pub. Date: Mar. 28, 1996--

Signed and Sealed this

Fourteenth Day of March, 2000

*Attest:*

*Attesting Officer*

Q. TODD DICKINSON

*Commissioner of Patents and Trademarks*